United States Patent
Herekar et al.

[11] Patent Number: 6,159,205
[45] Date of Patent: Dec. 12, 2000

[54] RADIATION TREATMENT METHOD FOR TREATING EYES TO CORRECT VISION

[75] Inventors: Satish V. Herekar, Palo Alto; Benjamin W. Woodward, Santa Clara, both of Calif.

[73] Assignee: Sunrise Technologies International Inc., Fremont, Calif.

[21] Appl. No.: 09/388,635

[22] Filed: Sep. 1, 1999

Related U.S. Application Data

[63] Continuation-in-part of application No. 09/146,999, Sep. 4, 1998.

[51] Int. Cl.$^7$ .................................................. A61B 18/18
[52] U.S. Cl. ............................. 606/17; 606/4; 606/10
[58] Field of Search ........................... 606/4–6, 10–17; 219/121.78–121.8; 356/358–363

[56] References Cited

U.S. PATENT DOCUMENTS

| | | | |
|---|---|---|---|
| 4,538,608 | 9/1985 | L'Esperance, Jr. | 128/303.1 |
| 4,665,913 | 5/1987 | L'Esperance, Jr. | 128/303.1 |
| 4,884,884 | 12/1989 | Werner . | |
| 4,887,019 | 12/1989 | Reis et al. . | |
| 4,887,592 | 12/1989 | Loertscher . | |
| 4,976,709 | 12/1990 | Sand . | |
| 5,000,563 | 3/1991 | Gisel et al. . | |
| 5,002,386 | 3/1991 | Reis et al. . | |
| 5,098,426 | 3/1992 | Skair et al. . | |
| 5,137,530 | 8/1992 | Sand . | |

(List continued on next page.)

FOREIGN PATENT DOCUMENTS

| | | |
|---|---|---|
| 0467775A | 1/1992 | European Pat. Off. . |
| WO 8707829 | 12/1987 | WIPO . |
| WO 8907920 | 9/1989 | WIPO . |
| WO 9011054 | 10/1990 | WIPO . |
| WO 9316631 | 9/1993 | WIPO . |
| WO 9403134 | 2/1994 | WIPO . |
| WO 9527534 | 10/1995 | WIPO . |
| WO 9818522 | 5/1998 | WIPO . |
| WO 9819741 | 5/1998 | WIPO . |
| WO 9822055 | 5/1998 | WIPO . |

OTHER PUBLICATIONS

Neumann et al. "Effect of Thermokeratosplasty on Corneal Curvature" Journal of Cataract Refractive Surgery, vol. 16, pp. 727–721, Nov. 1990.

Cartlidge et al., "A laser Surgical unit for Photoablative and Photothermal Keratoplasty", SPIE, vol. 1423, pp. 167–175, Jan. 21, 1991.

Thompson et al., "Therapeutic and Diagnostic Application of Lasers in Ophthalmology", Proceedings of the IEEE, vol. 80, No. 6, pp. 838–860, Jun. 1992.

(List continued on next page.)

*Primary Examiner*—Linda C. M. Dvorak
*Assistant Examiner*—Ahmed Farah
*Attorney, Agent, or Firm*—Majestic, Parsons, Siebert & Hsue PC

[57] ABSTRACT

An automated method is described for advantageously preparing and treating an eye of the patient. The method further provides a vision-corrective procedure, such as photothermal keratoplasty. The automated method is useful to dry the cornea to reduce or eliminate a tear film on the corneal surface that might otherwise interfere with or reduce the efficacy of a vision-corrective procedure and thereafter to treat the cornea according to a vision-corrective procedure. The automated method is user-friendly, allowing the treatment provider to develop or to select an appropriate pretreatment and treatment plan and to activate sane using a familiar "Windows" environment. The method has particular application in the area of automated corneal preparation and treatment, it may be used in the automated preparation and treatment of other tissues or substrates.

8 Claims, 8 Drawing Sheets

Microfiche Appendix Included
(2 Microfiche, 81 Pages)

U.S. PATENT DOCUMENTS

| | | | |
|---|---|---|---|
| 5,152,759 | 10/1992 | Parel et al. | 606/5 |
| 5,263,951 | 11/1993 | Spears et al. . | |
| 5,281,211 | 1/1994 | Parel et al. . | |
| 5,304,169 | 4/1994 | Sand . | |
| 5,318,047 | 6/1994 | Davenport et al. . | |
| 5,334,190 | 8/1994 | Seiler . | |
| 5,348,551 | 9/1994 | Spears et al. . | |
| 5,376,086 | 12/1994 | Khoobehi et al. | 606/4 |
| 5,395,356 | 3/1995 | King et al. | 606/4 |
| 5,437,658 | 8/1995 | Muller et al. | 606/5 |
| 5,439,462 | 8/1995 | Bille et al. | 606/6 |
| 5,520,679 | 5/1996 | Lin . | |
| 5,556,395 | 9/1996 | Shimmick et al. . | |
| 5,569,238 | 10/1996 | Shei et al. . | |
| 5,618,284 | 4/1997 | Sand . | |
| 5,779,696 | 7/1998 | Berry et al. | 606/16 |

OTHER PUBLICATIONS

Durrie et al., "Application of the holmium: YAG laser for refractive surgery", Reprint of paper to be published in SPIE Proceedings, 644, Nov. 1992.

International Search Report for PCT/US 99/20154 dated Jan. 13, 2000.

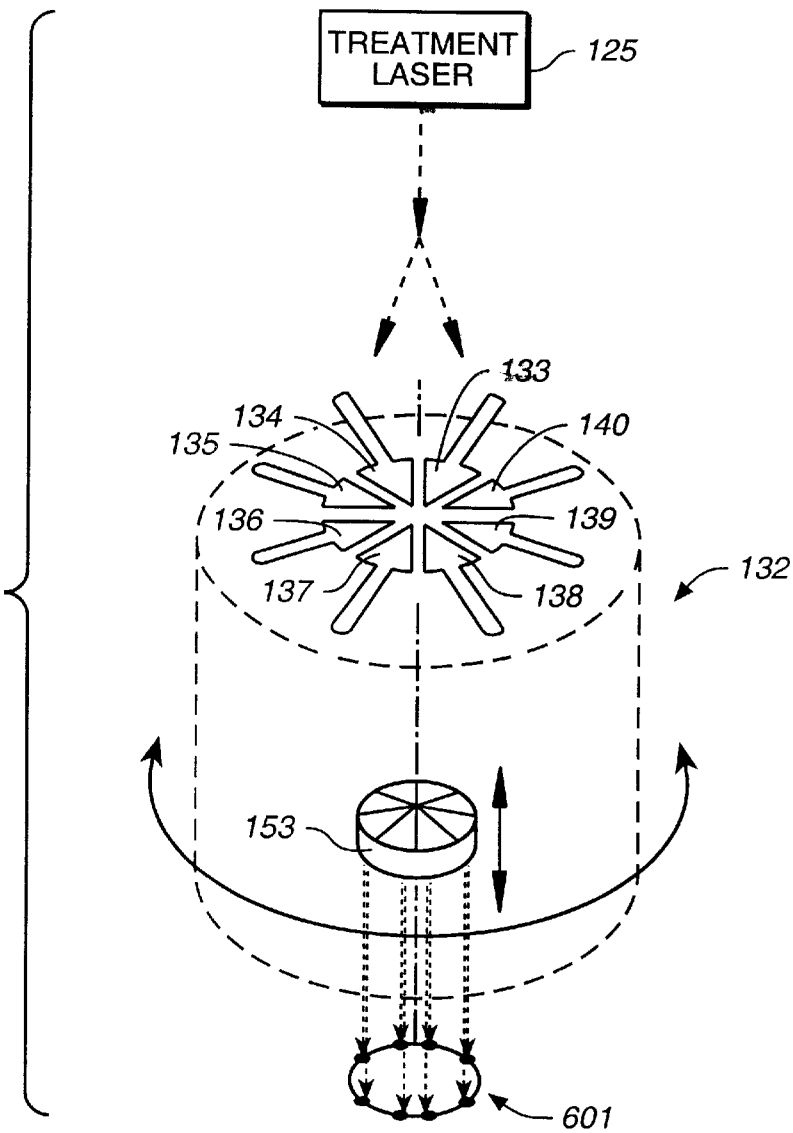
FIG._1
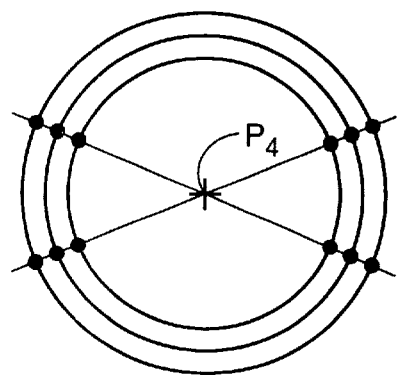
FIG._4C

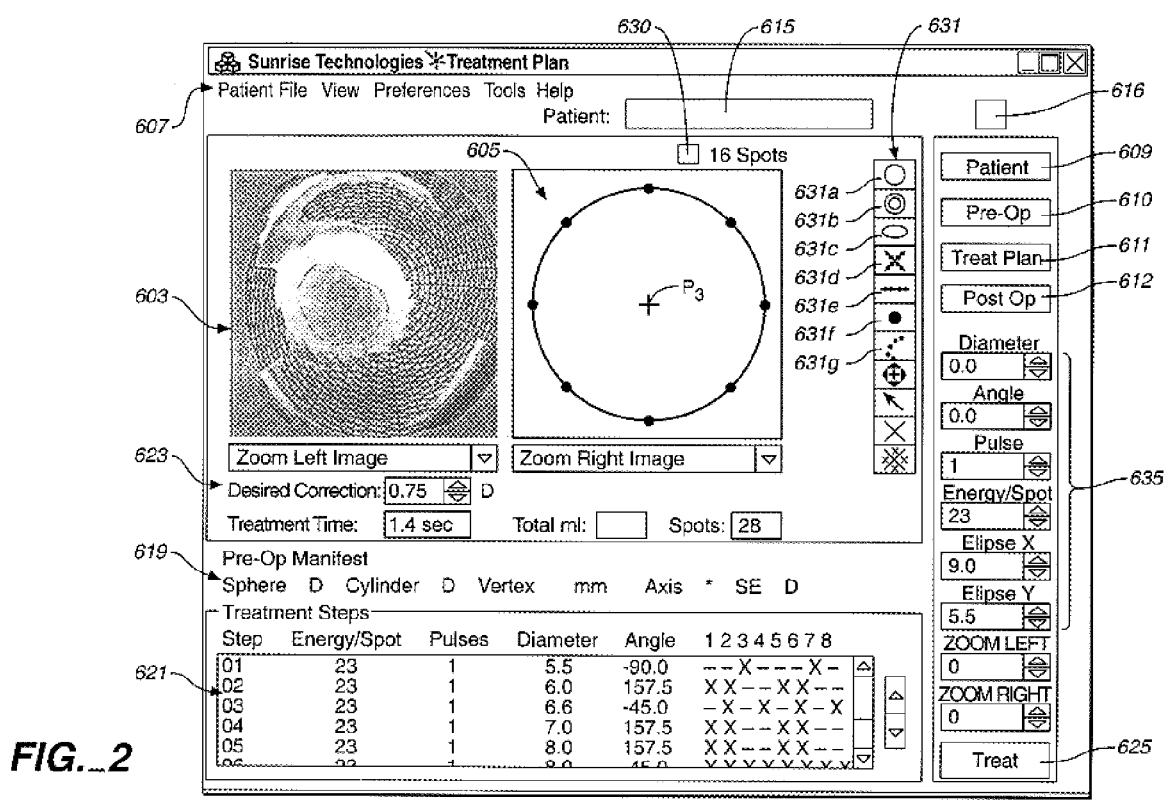
FIG._2

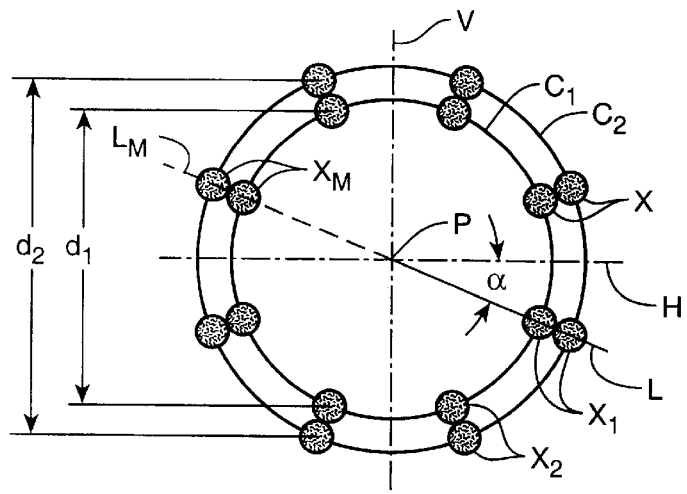
FIG._3
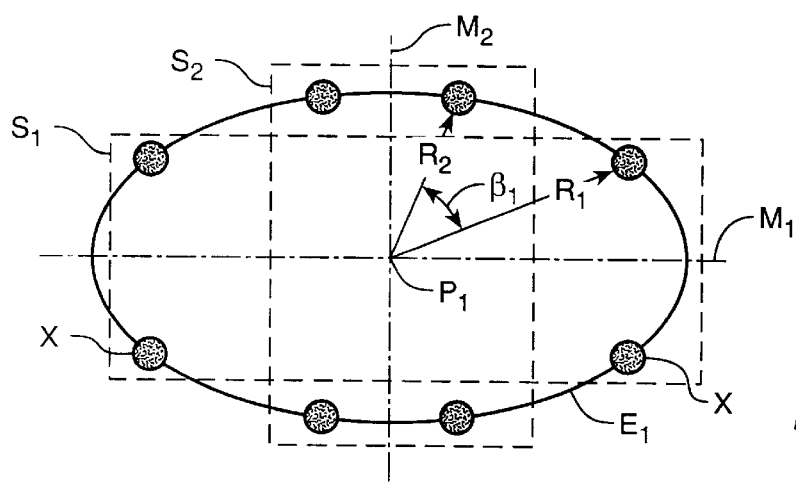
FIG._4A
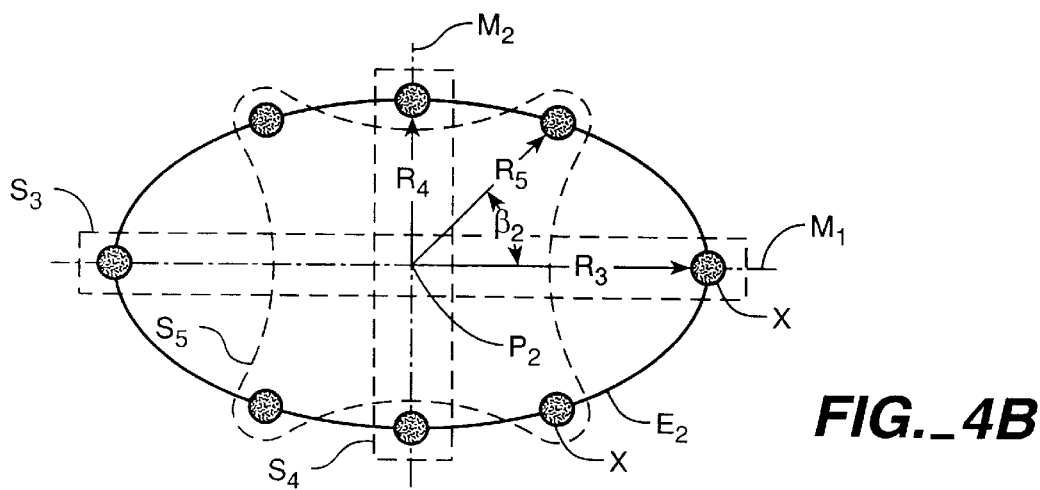
FIG._4B

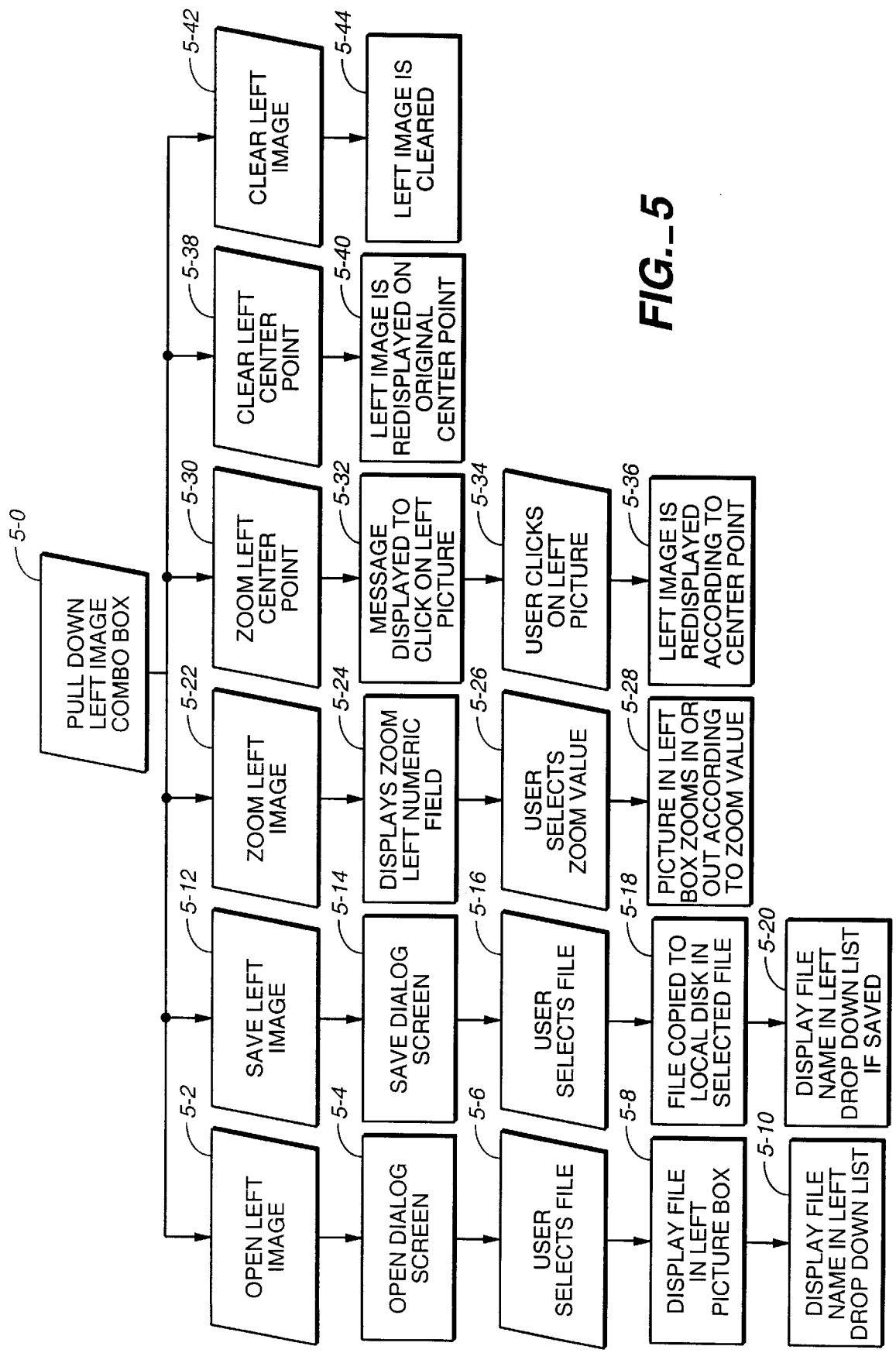
FIG._5

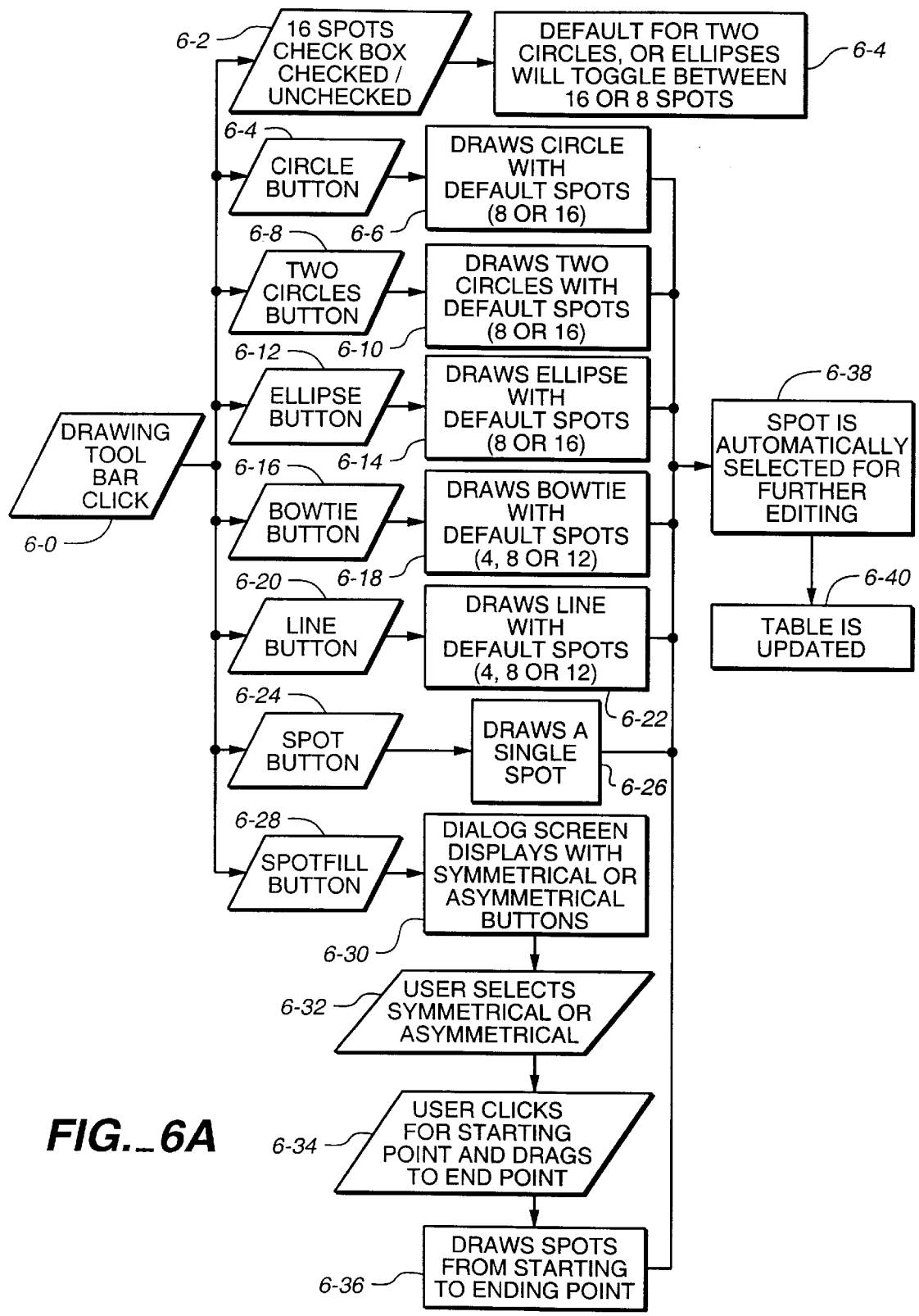
FIG._6A

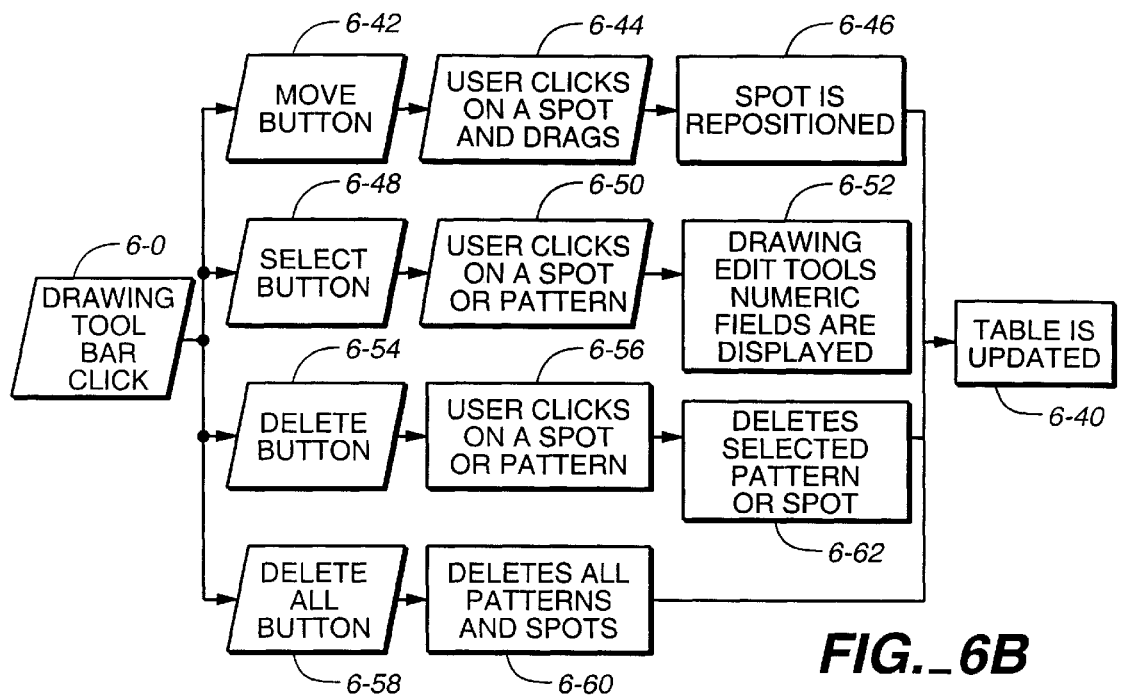
FIG._6B
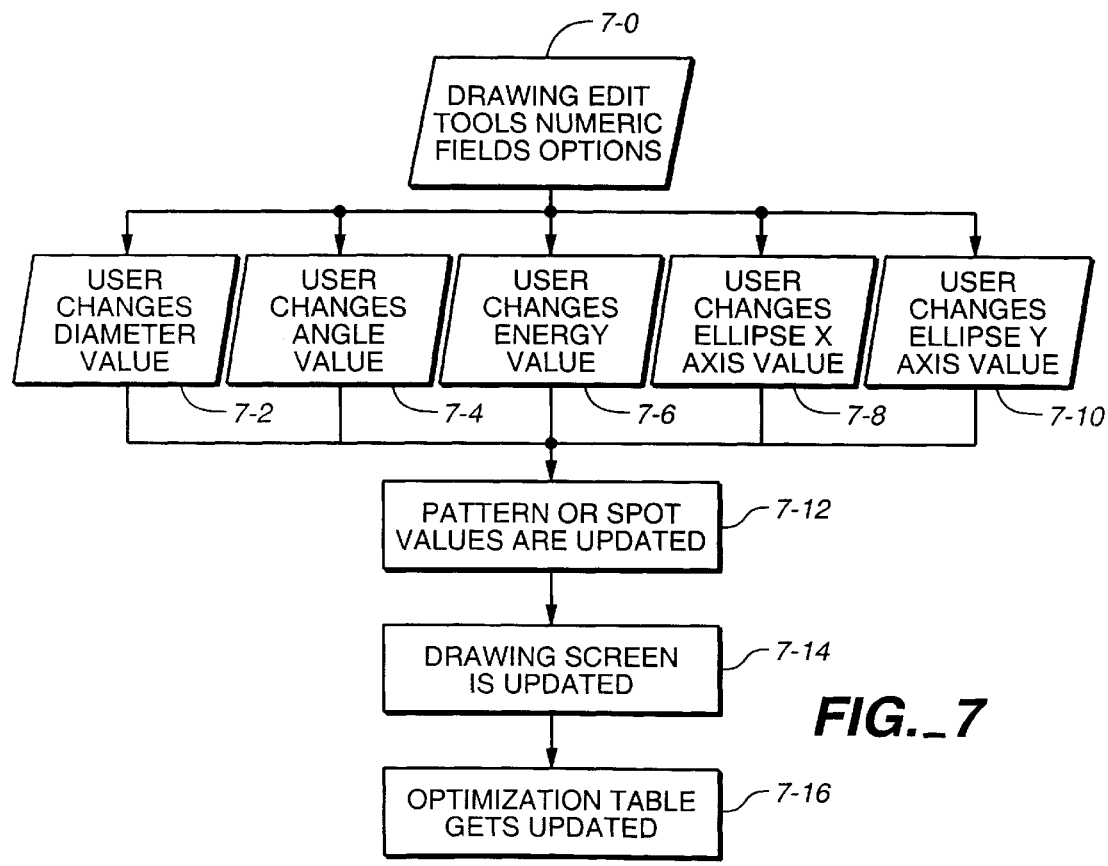
FIG._7

| COLUMN 1 | COLUMN 2 | COLUMN 3 |
|---|---|---|
| DATA DISPLAYED ACCORDING TO TABLE INFORMATION | TABLE CONTENT INFORMATION PER LINE | PRE-OP INFORMATION |
| TOTAL TREATMENT TIME | STEP NUMBER | SPHERE |
| TOTAL mJ | ANGLE | CYLINDER |
| TOTAL SPOTS | ENERGY | VERTEX |
|  | PULSES | SE |
|  | DIAMETER |  |
|  | SPOTS ON OR OFF (SHUTTERS) |  |
*FIG._8*
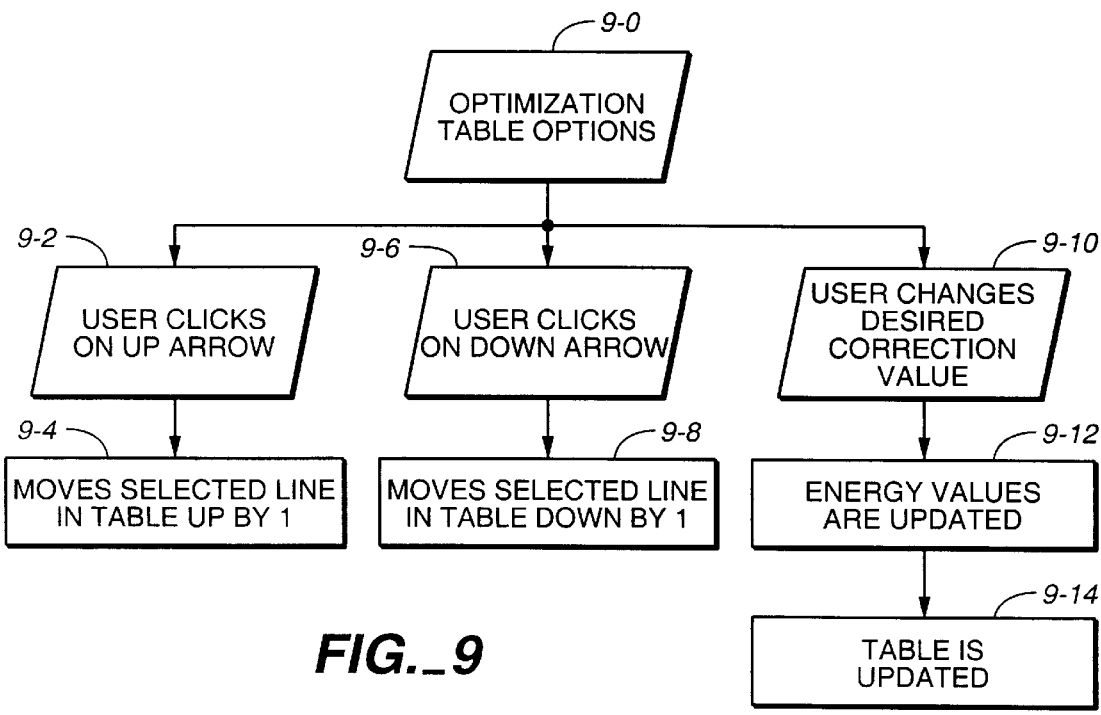
*FIG._9*

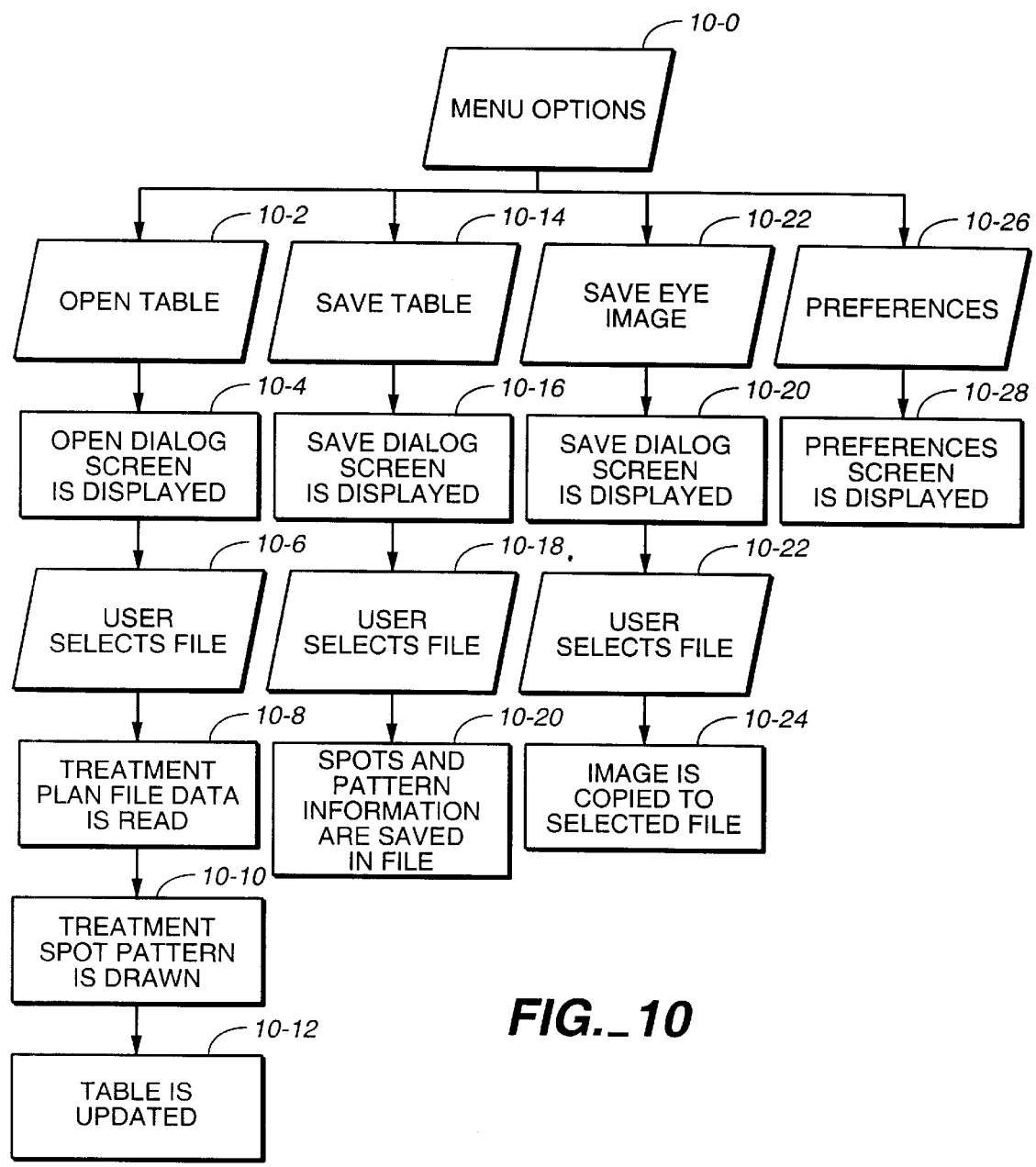
FIG._10

RADIATION TREATMENT METHOD FOR TREATING EYES TO CORRECT VISION

CROSS-REFERENCE TO RELATED APPLICATIONS

This is a continuation-in-part of co-pending U.S. patent application Ser. No. 09/146,999 (hereinafter, "First Co-Pending Application") of Herekar et al., filed on Sep. 4, 1998, pending, and entitled "METHOD AND APPARATUS FOR EXPOSING A HUMAN EYE TO A CONTROLLED PATTERN OF RADIATION."

This application is also related to a co-pending U.S. patent application Ser. No. 09/148,108 (hereinafter, "Second Co-Pending Application") of Herekar et al., filed on Sep. 4, 1998, pending, and entitled "APPARATUS AND METHOD FOR RECEIVING THE HEAD OF A SUBJECT, AND SYSTEM AND METHOD FOR TREATING TISSUE IN A REGION OF THE HEAD OF A SUBJECT"; and to a co-pending U.S. patent application Ser. No. 09/376,269 (hereinafter, "Third Co-Pending Application") of Herekar, filed on Aug. 18, 1999, pending, and entitled "APPARATUS AND METHOD FOR PREPARING AN EYE OF A SUBJECT, AND SYSTEM AND METHOD FOR TREATING EYE TISSUE OF A SUBJECT". These First, Second and Third Co-Pending Applications are expressly incorporated herein in their entireties by this reference.

REFERENCE TO A MICROFICHE APPENDIX

A microfiche appendix including two microfiche containing a total of 81 frames forms a part of the disclosure herein.

FIELD OF THE INVENTION

The invention relates generally to a coordinated system for treating the eye of a subject, and a method of using same. More particularly, this invention relates to a coordinated or automated system that is used to prepare the eye of a patient for medical treatment and to treat the eye, and methods associated with such a system. The system and method of using same are particularly useful in vision-correction applications, such as photothermal keratoplasty applications wherein a defined pattern of electromagnetic radiation is delivered to a cornea in a controlled manner for the purpose of reshaping the cornea. Although the various aspects of the present invention are primarily described with respect to corneal reshaping, they also have application to the treatment of bodily tissue other than found in the eye, such as to reshape an outside surface of such tissue.

BACKGROUND OF THE INVENTION

There are many specific treatment procedures which involve directing a highly controlled beam of electromagnetic radiation to an eye. For example, one specific surgical procedure that has been described involves using a radiation beam to ablate and thus cut portions of the corneal tissue. A specific application of this surgical procedure is in the performance of a radial keratotomy procedure, in which radial cuts are made in the cornea using a laser as opposed to a surgical knife. In another specific treatment procedure, an outside surface of the cornea is removed by an excimer laser in order to reshape it. Despite the existence of the aforementioned specific procedures, alternative "keratoplasty" procedures are currently receiving a great deal of attention because of their ability to correct for near-sightedness, far-sightedness and/or astigmatism.

In a particular keratoplasty procedure, which avoids cutting or ablating any portion of the cornea, at least one focused beam of electromagnetic radiation within the infrared portion of the spectrum is directed into the eye to shrink collagen tissue within the cornea in order to cause corrective changes in corneal curvature. This technique, often termed "photothermal keratoplasty", "laser thermal keratoplasty", or "laser thermokeratoplasty" is the subject of U.S. Pat. Nos. 4,976,709 and 5,618,284 to Bruce J. Sand (hereinafter, "the Sand Patents"), where the technique is described to be carried out with a holmium:YAG laser. The Sand patents are expressly incorporated herein in their entireties by this reference. This collagen shrinkage technique promises to provide permanent changes to the optical characteristics of the human cornea with a higher degree of safety and patient comfort than that provided by techniques that involve physically cutting and removing portions of the cornea.

One way to deliver a desired electromagnetic radiation pattern to the cornea is by projection from a short distance removed from the cornea. One instrument for doing so is described in the Published International Patent Cooperation Treaty Application WO 94/03134 (hereinafter, "the PCT Publication"), which publication is expressly incorporated herein in its entirety by this reference. This instrument allows an ophthalmologist, or other attending physician or practitioner, to select and to deliver a specific pattern and amount of electromagnetic radiation to each patient in accordance with the condition to be corrected. It is desirable for such an instrument to perform efficient corrective photothermal keratoplasty procedures on a large number of patients with a high degree of accuracy, effectiveness, safety and convenience.

The aforementioned Third Co-Pending Application discloses apparatus and methods for applying a flow of a conditioning or drying medium to an external surface of an eye of a patient, to dry the eye in preparation for ophthalmological observation and/or treatment. Such apparatus and methods are particularly useful in to prepare a patient's eye for vision-corrective ophthalmological treatments, such as photothermal keratoplasty, wherein a defined pattern of electromagnetic radiation is delivered to an external surface of the cornea in a controlled manner for the purpose of reshaping the cornea. The aforementioned First and Second Co-Pending Applications describe a system and methods for using the system to expose an eye of a patient to a controlled pattern of radiation and for holding the head of the patient in preparation for and during such exposure.

It is desired to make the exposure system as automated as reasonably possible for determining a pattern of radiation exposure that is appropriate to correct the vision of a particular eye of a patient, for preparing the eye for such an exposure and for then exposing the patient's eye to that pattern of radiation, all with convenience and efficiency for an attending physician or other provider of the treatment.

SUMMARY OF THE INVENTION

An improved treatment system provides graphical displays and calculation features that improve the ease with which the treatment provider (system user) may determine a pattern of one or more radiation exposures for each specific patient's eye or other area of tissue to be reshaped, and then carry out those exposures. A library of potential radiation patterns may be made available to the treatment provider from which one or more may be chosen as the provider forms a specific treatment pattern for use in reshaping tissue, a particular application being to correct the vision of a particular eye by reshaping the outer surface of its cornea. A treatment radiation pattern is preferably graphically displayed as it is formed from one or more of the library patterns and/or by characteristics directly inputted by the treatment provider. It is desirable that various parameters of the chosen library patterns be alterable by the treatment provider to conform the resulting pattern to what is necessary for the specific area of tissue being treated. The treatment provider may import and display a topographical or other diagnostic image of the patient's cornea, or other tissue area to be treated, for use in developing a treatment plan for that area. This image may be displayed on the system screen adjacent to an area where the radiation pattern being constructed is graphically displayed, or the treatment radiation pattern may be constructed directly over the diagnostic image. This allows the treatment radiation to be closely conformed to the condition of the eye or other tissue to be reshaped.

An example of an instrument described herein for exposing tissue to the specified treatment pattern is characterized by exposing the tissue at one time to a pattern of spots equally spaced around a circle with an adjustable diameter. The spots are rotatable around the circle, and are individually selectable for an exposure. Once a treatment pattern is graphically constructed on the system screen and its parameters selected, the system automatically specifies one or more such exposures which together give the desired treatment radiation pattern.

Additionally, improved techniques are provided for determining optimal patterns of radiation for treating specific areas of tissue. Included are patterns that correct for astigmatism in the cornea of an eye. Elliptical patterns of radiation spots, for example, have been found to provide good correction for astigmatism and hyperopia at the same time. In specific embodiments, elliptical patterns of radiation spots are formed from either two circles of spots having different radii, or from a combination of one circle of spots and two pairs of linearly arranged spots along orthogonal axes. A bow tie arrangement of spots has also been found useful for correcting for astigmatism alone. It is desirable that appropriate ones of these techniques be used along with the graphical display features described in the preceding paragraph but they may also be used alone.

Additional aspects, advantages and features of the present invention will become apparent from the description of preferred embodiments, set forth below, which should be taken in conjunction with the accompanying drawings, a brief description of which follows.

BRIEF DESCRIPTION OF THE DRAWINGS

FIG. 1 is a schematic representation of the optical arrangement of the ophthalmic treatment system of the First Co-Pending Application identified above to form controlled patterns of treatment radiation;

FIG. 2 is an example screen display used to develop a treatment radiation patterns of a specific patient's eye;

FIG. 3 is an illustration of a treatment plan pattern of radiation spots arranged in two concentric circles;.

FIGS. 4A and 4B are illustrations of treatment plan elliptical patterns of radiation spots formed of multiple exposures, wherein sets of spots within the patterns are indicated by broken lines;

FIG. 4C is an illustration of a treatment plan pattern of radiation spots arranged in a bow tie pattern;

FIG. 5 is a flow chart that illustrates a method of using and manipulating an image on the system display, such as a diagnostic image of a patient eye;

FIG. 6 is a flow chart that illustrates a method of developing a treatment plan radiation pattern, which may be any of a variety of treatment patterns;

FIG. 7 is a flow chart that illustrates a method of changing parameters of a treatment plan spot or pattern;

FIG. 8 is a table that shows information display fields that may be displayed to the user using the system computer and software therefor;

FIG. 9 is a flow chart that illustrates a method of interacting with a table that displays data concerning a treatment plan pattern; and FIG. 10 is a flow chart that illustrates a method of accessing and manipulating data to facilitate the planning of a treatment pattern.

DESCRIPTION OF SPECIFIC EMBODIMENTS

Referring initially to the diagram of FIG. 1, primary optical elements utilized to form a circular pattern 601 of eight radiation spots, as a specific example, is shown. Radiation from a source 125, such a laser, is directed to a sub-assembly 132 that includes eight triangularly shaped shutters 133–140, one for each of the eight radiation spots that may be generated. These shutters are all shown to be closed, and include control motors (not shown) that individually operate the shutters between opened and closed positions. The sub-assembly 132 also contains a polyprism 153 that has eight substantially flat surfaces on one side that forms a pyramid, one of the eight treatment spots being formed from each of the flat surfaces. Radiation from the laser 125 is directed against the shutters and then, for those shutters that are opened, onto respective flat surfaces of the polyprism 153, through the polyprism and then through other optical elements not a part of the sub-assembly 132, and onto the patient's eye as a radiation pattern of up to eight spots. The eight spots are equally spaced around a circle. Of course, more or fewer than eight spots may be made available by use of a polyprism with a different number of flat surfaces, at least four such spots usually being desired.

For any particular treatment radiation exposure, the number of spots is controlled by opening the individual shutters 133–140 corresponding to the desired spot locations. The radius of the circle of spots 601 is controlled by moving the sub-assembly with respect to the laser 125. The angular positions of the spots around the circumference of the circle are controlled by rotating the sub-assembly 132. Additional details of the delivery optics and an associated control and operating system are given in the First Co-Pending Application referenced above.

The wavelength of radiation used for the treatment, its magnitude and the duration of the exposure, are selected to be adequately absorbed by the corneal or other exposed tissue to raise its temperature at the exposed spots to a level sufficient so that the tissue changes in the manner desired. When used to reshape the surface of the cornea or other tissue, the preferred technique is to control these parameters to cause tissue below the surface to change in a manner that reshapes the surface, without ablating the exposed tissue. The radiation wavelength is usually selected from the infrared or near infra-red portions of the spectrum. However, the instruments and techniques described herein are also applicable to other processes that require exposure to radiation patterns with different parameters.

The above-described system is applied in this description to correct abnormal refractions of a patient's eye by delivering energy in a pattern of spots to the patient's cornea such that the curvature of the cornea is modified. The system can be used for a variety of refractive conditions, including astigmatism, and is particularly useful in the treatment of hyperopia wherein the curvature of the cornea is steepened to increase the refractive power of the cornea. Whatever the initial condition of the cornea, the treatment provider considers that condition, chooses an appropriate treatment plan, and treats the patient accordingly.

An example screen display used by the treatment provider to design and execute a treatment plan for a patient's eye is shown in FIG. 2 ("Treat Plan" screen). A central aspect of the display is the provision of two image boxes, a left image box 603 and right image box 605. In the example of FIG. 2, topographical representation of a patient's eye prior to treatment is displayed in the left box 603, and the pattern of radiation spots developed by the treatment provider (user) as part of a treatment plan for that eye is displayed in the right box 605. An important feature of the system being described is that the images of both of these boxes may be combined into one, thus enabling the user to designate the placement of radiation exposure spots at location across the eye where they will do the most good. Other items on the screen display of FIG. 2 are included in later descriptions of uses of the screen.

The planning of an appropriate vision-modification treatment and the carrying out that treatment is preferably interactive and automated, as further described below, using software that can be run on a desktop computer included as part of the ophthalmic treatment system. The primary interface is the touch screen display described above, which both provides information to the treatment provider (user) and accepts input commands from the user touching appropriate areas of the screen. A keyboard and a trackball, or a mouse, also provide a familiar method of data and command entry. The laser is preferably activated by using a foot switch, thus freeing the user's hands for interfacing with the touch screen, keyboard, trackball, and the patient. Additional details of the treatment system are given in the First Co-Pending Application reference above.

The system software preferably utilizes screen displays and formats that are familiar or convenient to the user. By way of example, the software preferably uses "Windows"-type features, including layouts, menus, and control buttons, or icons, that are familiar to many, if not most, computer users. A control button on the screen may be activated physically, by touching or pressing the screen over the button, or by using the trackball to locate a screen pointer over the button and clicking an activation button on the trackball housing, as will be familiar to the user. The keyboard is used to enter patient information, treatment parameters, and the like.

Electrical power is preferably connected to the ophthalmic treatment system by activating a key switch, whereupon the system undergoes an automatic self-test. If the system fails the self-test, an alert, audio or otherwise, will be activated, and a system error will be indicated on the heads-up display. If the system passes the self-test, an initial screen or a main screen will appear on the touch screen display.

Typically, when the primary power is supplied to the system, the interactive tools of the system, such as the touch screen, trackball, and keyboard, are turned "on". An initial "user log on" screen may be used for entry of the user's identification and password information to access the further screens and menus for patient-specific data entry, treatment planning, treatment, and the like. Once access is provided, a main screen that includes a button panel, a main menu, a toolbar, and a status bar appears. The user interacts with these features in a known manner using the interactive tools provided.

The status bar simply contains information concerning the status of the system software, such as what screen is open for use, as generally known. The toolbar contains typical "Windows"-type control buttons, or icons, for "New", "Open", "Save", "Print", and "Help". Other icons may be included, such as the edit options of "Cut", "Copy", "Paste", and the like.

The main menu typically offers "Patient", "View", "Preferences", "Tools" and "Help" pull down menus, in an area 607 of the screen of FIG. 2. The "Patient" menu generally allows for selecting among the entry of patient-specific data, the opening of an existing patient data file, the saving of a patient data file, as well as exiting from the "Patient" menu. The "View" menu generally allows for toggling the status bar "on" and "off" and for making other choices affecting the form or content of the display. The "Preferences" menu typically allows for unit selection, such as metric units or other preferred units, for eye-chart preference selection, and for instrument- and treatment-preference selection. The "Tools" feature typically allows one to access service programs, or to connect to an Internet site, as described in the First Co-Pending Application referenced above, for enabling procedures. The "Help" menu generally allows the user to view information of the use of the software.

The button panel of many screens, such as the screen of FIG. 2, typically includes "Patient", "Pre-Op", "Treat Plan" and "Post Op" input buttons 609–612, respectively. When touching or clicking upon the Patient or Pre Op buttons 609 or 610, the treatment provider may create or view a patient file that includes the patient name, the identification of the left or right eye, and the pre-operative examination date. The screen of FIG. 2 displays the patient name and left or right eye in spaces 615 and 616. This patient file helps the user confirm that the pre-operative data is sufficiently current to serve as a basis for treatment planning, and that the treatment plan, treatment, and the post-operative information relate to the correct patient and the correct eye of that patient. Thus, preferably, the software is designed to require the creation of this patient file before the Treat Plan or Post Op features are made available to the user.

As mentioned above, the patient file is created using the Patient and Pre-Op features. The Patient feature allows for the entry of patient-specific data, such as the patient name or other identifier, birth date, gender, contact data, and the like, or the viewing, editing, or saving of same. Preferably, the software is designed to require entry of either the patient name or identification, birth date and gender to create the patient file before the user may employ the Treat Plan or Post Op features.

The Pre Op feature allows the user to enter, view, edit, or save pre-operative examination data, such as the date of the examination and the name of the examiner; identification of the left or right eye; refractive information, for example, sphere (diopters) and cylinder (diopters), axis (degrees), and vertex (mm) for manifest, cycloplegic, and auto-cyclopegic; keratometry information, for example, steepness reading, flatness reading, and axis reading; other physical parameters of the eye, such as intraocular pressure (IOP, mmHg), pachymetry ($\mu$m), and pupil diameter (mm); and standardized visual acuity charts, including uncorrected visual acuity (UCVA), best corrected visual acuity (BCVA), and uncorrected near visual acuity (UNVA), that can be selected in the Preferences pull down menu. A notes or commentary field is also provided for the examiner to enter text concerning the examination. Preferably, the software is designed to require entry or selection of the left or right eye of the patient to create the patient file.

Once the patient file is created, it may be used to assist the user in planning a vision-modification treatment for the selected eye of the patient. The user will verify certain information in the patient file, such as the patient name or identification and the eye to be treated, before accessing the Treat Plan feature for such planning.

The Treat Plan screen (FIG. 2 is an example of such a screen) may be accessed to view a treatment plan that has already been performed. In this case, the user will not be allowed to make changes in the Treat Plan screen. Alternately, the Treat Plan feature may be accessed for the planning of a new treatment. If the pre-operative examination data has already been entered for the patient eye to be treated, as described above, the Treat Plan screen will show the refractive data in a region 619 to assist the user in treatment planning. The manifest, cycloplegic, or auto-cycloplegic refractive data may be viewed according to a user's selection in the Preferences menu described above.

Based on the refractive data in the Pre Op data file, a treatment plan (nomogram) is generated according to algorithms and default values provided in the system software. For example, the treatment plan including spots X (such as $X_1$, $X_2$, etc.) arranged in two concentric circles $C_1$ and $C_2$ of eight spots each may be generated, as shown in FIG. 3. The treatment plan also includes a desired correction, such as a spherical equivalent in diopters and an angle in degrees, that is generated from algorithms in the system software. The angle may be explained as follows. When a vertical axis V and horizontal axis H are drawn through the effective center point P of a proposed treatment pattern, the angle $\alpha$ corresponds to the angular separation between the horizontal axis H to the right of the center point P and a line L drawn from the center point through the first spot $X_1$ in the pattern beginning on the horizontal axis and moving in the clockwise direction therefrom. Preferably, the angle is from about zero (for example, if the first spot is on the horizontal axis) to about 45 degrees. For example, in the treatment pattern shown in FIG. 3, the angle $\alpha$ is about 22.5 degrees.

The treatment plan also includes the treatment parameters, such as the number of treatment steps, and for each step, the amount of energy (mJ) per spot, the number of energy pulses, the dimensions of the treatment pattern, those of the 8 possible spots which are to be used, and the like. The treatment plan is displayed in a region 621 of the screen of FIG. 2, where each line provides the parameters for a single exposure and the exposures are listed in the order that they are to be made. In the example just given with respect to FIG. 3 (not that shown in FIG. 2), there are two treatment exposures, one for the spots of each circle. For the first exposure, the parameters include 28 mJ per spot, 7 pulses, an effective pattern diameter $d_1$ of 6 mm, and all 8 of the spots being turned on. For the second step, the same or different energy per spot, the same or different number of pulses, a different effective pattern diameter $d_2$, such as 7 mm, and all 8 spots. The software also optionally allows the user to simulate a treatment to get a simulated experience of how the treatment plan will be carried out.

In a specific example, in response to the user selecting a double circle pattern, the software generates spots in the two circles of FIG. 3 with respective diameters of 6 mm and 7 mm. Two exposures are necessary if 8 spots are in each circle, one exposure for each of the two circles. Four exposures are necessary if each circle has 16 spots. It is the energy level of the radiation spots in a predefined pattern that is varied to bring about the amount of tissue surface reshaping that is desired for a particular patient. When applied to a particular eye, the amount of desired correction $\Delta SE$ is determined by the physician and inputted in a field 623 (FIG. 2) to the system. The system software then calculates the amount of radiation energy that should be delivered to the cornea of that eye. For 8 spots in each circle, the total amount of energy, in mJ, for 8 spots is set equal to $237+(44.25)(\Delta SE)-(0.60)$(patient age). The patient age is among the data that are inputted to the system for each patient that is treated. For 16 spots in each circle, the total amount of energy, in mJ, for each 8 spots is set equal to $238+(15.95)(\Delta SE)-(0.40)$(patient age).

The treatment plan of a specific series of exposures is preferably alterable by the user after it is developed, especially when the plan has automatically resulted from execution of an algorithm in the system software from an entry of little more by the user than the desired correction in a display field 623 (FIG. 2). The user may interactively change this desired correction after a treatment plan has been established and view the new spot pattern replacing the old pattern in the right display box 605. When a changed correction is made by the user, the treatment plan is updated and re-calculated by the system software. In addition to the new pattern being displayed in the box 605, the details of the exposure steps displayed in the region 621 are updated. Alternately, the user may change certain specifics of the listed exposure steps by clicking on them and manually changing their values. This also results in the spot pattern displayed in the box 605 being updated if any changes affect the pattern.

Once the treatment plan is finalized, the user or treatment provider may prepare to treat the selected patient eye. Generally, the user ensures that the treatment plan information is correct. The user then presses a "Treat" control button 625 to gain access to a Treatment screen. Using the Treatment screen, the user may prepare the eye for treatment and commence treatment.

Typically, the user will precondition or dry the eye. Preferably, the eye is dried to reduce or eliminate a tear film that may otherwise compromise or interfere with the corneal-modification treatment. The upper and lower eyelids may be held out of the corneal area, for example, using a speculum, to facilitate eye-drying. The eye may be dried using a flow of drying medium, such as warm (about 45° C.), dry air ($\leq$about 15% relative humidity), for a period of from about 7 seconds to about one minute, and preferably, from about 15 seconds to about 30 seconds, as described in the Third Co-Pending Application. Preferably, the temperature and relative humidity are well-controlled, as may be accomplished using the conditioning system described in the above-mentioned application. This is the preferred conditioning method, as it minimizes eye-preparation time and provides substantially uniform eye-drying. Alternately, the eye may be dried naturally by the presence of ambient air in the vicinity of the eye over a period of time, such as three minutes. Natural drying is not preferred given the time involved and the lack of control over the ambient conditions, which may affect drying uniformity, and thus, the treatment outcome, and repeatability from one treatment to other treatments.

Whether the eye is dried naturally or using an eye-drying device, the user activates an eye-drying start control button to start a timer to time the eye-drying process. A default time for eye-drying may be selected in the Preferences pull down menu described above. Preferably, a drying-time countdown will appear in the Treatment screen, either showing the time remaining or the time that has expired in the eye-drying process.

Typically, the user activates an automatic calibration of the system, as described in the First Co-Pending Application referenced above, while the eye-drying is taking place. The automatic calibration process may be activated using an auto-calibration control button on the Treatment screen. In the automatic calibration process, the system preforms a series of system calibrations and checks. Preferably, the Treatment screen includes a progress bar to show the progress of the automatic calibration and its success or lack of success. If the automatic calibration is unsuccessful, an explanatory message will be displayed and treatment will not be allowed. If the automatic calibration is successful, the user may proceed further with treatment preparation and treatment.

If a headrest is used with the system, as is preferred, the user will position the patient's head appropriately with respect to the headrest. A headrest assembly and its use are described in the Second Co-Pending Application referenced above. If a headrest is not used, the user will position the patient's head appropriately with respect to the ophthalmic treatment instrument. The user may then focus the microscope of the ophthalmic treatment instrument on the patient's eye, align or center the treatment pattern with respect to the eye, and look for an indication that the system is "Ready". The Ready indications may appear on the heads-up display, as described in the First Co-Pending Application referenced above, and on the Treatment screen display in the form of an enabled Ready button. These Ready indications will appear or be enabled only when the automatic calibration has been successful and the eye-drying time has expired. If treatment is not performed within a certain time, such as about one minute, after the drying time expires, or within a certain time, such as about five minutes, after the automatic calibration is successfully completed, treatment of the eye will not be allowed. In such a case, the user will have to repeat the steps described above in preparation for treatment.

Once the system is in a Ready mode, the laser will be activated to deliver radiation continuously at the desired energy level while the safety shutter is closed to ensure that no energy reaches the patient. The user may set-up, check, or refine the head-positioning and the focusing and aligning of the ophthalmic treatment instrument with respect to the eye, as described above, prior to proceeding with treatment. By way of example, preferably the user will make sure the eye is within the visual field of the microscope, will confirm or adjust the centering of the treatment pattern with respect to the eye, and will confirm or adjust the focus so that two focus spots from a focusing laser (frequency doubled Nd:YAG or HeNe laser, for example) are brought together on the anterior surface of the cornea, as described in the First Co-Pending Application referenced above. Preferably, the user will also make sure that the head positioning is appropriate for treatment. For example, if a headrest assembly is used, the user will make sure the patient's head is pressed against the headrest, as described in the Second Co-Pending Application referenced above.

The user may now begin treatment by activating a foot switch and maintaining it in an activated state to open the safety shutter and start the treatment, as described in the First Co-Pending Application referenced above. A "Treatment" indication will appear in a heads-up display viewable to the user when viewing the eye of the patient. Optionally, the user may activate an eye-tracker system to monitor eye movement during treatment, as described in the First Co-Pending Application referenced above, using an eye-tracker control button on the Treatment screen. The eye-tracker system monitors the eye during treatment, and, if the eye has moved more than a pre-defined amount (0.6 mm for example) since the delivery of the first treatment pulse, places the treatment procedure in a pause mode.

During treatment, the laser delivers radiation at the energy level specified for the first step in the treatment plan, for the specified number of pulses in the specified treatment pattern. This is shown to be the first line of the exposure data displayed in the region 621. The remaining exposures, one line at a time in order, are performed automatically by the system, one at a time, according to the treatment parameters specified for each exposure. The system automatically adjusts itself between exposures to provide the appropriate energy, number of pulses, angle $\alpha$, circular diameter, selection of spots and the like, according to the data stored fore each of the exposures. This process is continued until all the specified exposures have been completed, at which time the eye has been treated according to the treatment plan.

Preferably, the Treatment screen shows the progress of the treatment by including the display 621 of the exposure steps with highlighting or some other marker indicating which of the lines of individual exposures is currently being, or just has been, made. The Treatment screen may also include a progress bar to show the progress of the treatment, for example, as a treatment-completion percentage. The Treatment screen may also include a status line for displaying prompts and messages to the user.

The user may put the treatment into a pause mode before all of the exposures have been made by deactivating the foot switch such that laser firing stops. The status of any pause may be displayed on the Treatment screen, such as the fact of the pause, the time elapsed in the pause mode, and the like. When the treatment is in a pause mode, the last exposure to have been made is highlighted in the display 621 and the progress bar, if any, shows the progress of the treatment until the pause mode took effect and will not show further progress until the treatment is resumed. Preferably, the Treatment screen will display a message providing brief instructions for resuming treatment. Treatment may be resumed by activating the foot switch within a certain time, such as ten seconds. If the treatment is not activated within the specified time limit, the system will go into a standby mode.

The treatment may also go into a pause mode if excessive eye movement is detected by an eye-tracker, if included in the system, as described above, or if the patient's head is moved out of an appropriate position with respect to the headrest assembly, as described in the Second Co-Pending Application referenced above. The user may decide to proceed with or without the eye-tracker, or with or without the head positioned appropriately with respect to the headrest assembly, respectively. To implement these decisions, the user either accepts the default mode or overrides the default mode using the interactive tools provided.

At the end of the treatment, a safety shutter is closed to prevent any further exposure to the laser radiation. Preferably, the treatment particulars are logged to the patient file, along with calibration data. The software system provides for the automatic archiving of patient and treatment data on a system hard mass storage disk drive. The system will provide a warning to the user if the archiving capacity drops below a certain level, such as 100 megabytes.

The user may create a post-operative examination record, using the Post Op feature. To create such a record, the user opens a patient file for the eye under examination and verifies that certain information in that patient file, such as patient name or identification and left or right eye, is correct. The user then presses or clicks upon the Post Op button 612 to bring up the Post Op screen. The Post Op screen will be blank if no previous data has been entered, or will display the data from the last Post Op record created for that particular patient eye. The Post Op feature allows the user to enter post-operative examination data using substantially the same data fields, such as examination date and examiner, refractive data, keratometry, visual acuity charts, IOP, pachymetry, and the like, as described above with respect to the Pre Op feature. A pupil-diameter data field may be omitted, as the treatment should not cause any alteration (other than normal alterations depending on conditions such as light) in the diameter of the pupil of the patient's eye. A comparative data field may be added to display a change in refractive data since the last refractive examination. Notes may be entered in a similar manner to that used for the Pre Op notes or commentary feature.

The Post Op feature may also include a "Graph" option for showing the patient's progress based on pre-operation and/or post-operation data. For example, the graph may display refractive data, such as manifest refraction in diopters, chronologically from the date of the pre-operative examination to the date of at least one post-operative examination. Preferably, the graph is a Cartesian plot, with the refractive data (in±diopters, for example) plotted with respect to the y-axis and the time data (in days, for example) plotted with respect to the x-axis.

As mentioned above, the Preferences menu maybe used to set several system parameters and defaults according to the user's preference. The Preferences menu may include several files, one for each preference category. For example, the Preferences menu may include an "Eye Chart" file in which the user selects a visual acuity chart, such as a UCVA, BCVA, or UNVA chart. Once selected, these eye charts will be available by initializing the Pre Op or Post Op feature. The Preferences menu may include a "Refractions" file in which the user selects which refraction values from the Pre Op feature, namely, manifest, cycloplegic, or autocycloplegic, will appear on the Treat Plan screen and be compared in the Post Op comparative data field.

The Preferences menu may include an "Options" file in which the user selects various operational parameters, such as system defaults. For example, the user may select between "on" and "off" for the heads-up display, the eye-tracker, the aiming laser, the focusing laser, and the setting of a pause between treatment exposure steps. The user can override the eye-tracker default during operation, as previously described. In the Options file, the user may also set a default time for drying the eye before treatment. The Preferences menu may also include a "Date and Time" file, wherein the user selects a date format, such as month/day/year or day/month/year format, and a time format, such as a.m./p.m. or 24-hour format, and sets or adjusts the date and time, accordingly.

As described in the First Co-Pending Application referenced above, the system may be activated to enable an ophthalmic treatment procedure using the Internet or laser enablement cards. A Main screen displays an enablement value corresponding to the number of treatments that can be enabled. Each time a complete treatment is performed, the number of treatments remaining is reduced by one. Preferably, once the number of treatments remaining reaches ten, a reminder message is displayed. Once the number of treatments remaining reaches zero, no further treatments are allowed. As mentioned above, laser enablement cards may be used for system activation. Such a card is inserted into the system, as described in the First Co-Pending Application referenced above. Preferably, a laser enablement card can activate the system to enable only one procedure.

While FIG. 3 illustrates a possible treatment plan pattern, namely, a pattern of spots arranged in concentric circles, many other treatment plan patterns may be developed according to the present invention. A pattern illustrated in the display box 605, for instance, is a pattern of all eight spots arranged in a single circle. In addition, elliptical treatment plan patterns, such as those shown in FIGS. 4A and 4B, may be developed, particularly for the treatment of astigmatism at the same time that hyperopia is being corrected. These elliptical patterns may be achieved by arranging treatment spots in circular patterns of varying circular diameter (or radius) and effectively removing certain treatment spots from each of the circular patterns. The treatment plan is carried out by using the shutters 133–140 of the ophthalmic treatment system (FIG. 1) to prevent radiation delivery from certain spot locations in each circular pattern.

FIG. 4A illustrates an elliptical pattern $E_1$ of eight spots X. Throughout the pattern, adjacent spots are separated by an angle $\beta_1$ of 45°. The pattern is arranged such that two sets $S_1$ and $S_2$ of four spots are arranged symmetrically with respect to the major axis $M_1$ and minor axis $M_2$. The four spots in each of the sets are made up of two pairs of spots that are directly adjacent one another in the treatment pattern. In each of the sets, one of the two pairs of directly adjacent spots mirrors the other. For each set, each of the spots in the set is the same distance from the center point $P_1$. For example, each of the spots in set $S_1$ is a radial distance $R_1$ from the center point and each of the spots in set $S_2$ is a radial distance $R_2$ from the center point. $R_1$ and $R_2$ are defined by and may be determined from the equation for the ellipse $E_1$.

FIG. 4B illustrates another elliptical pattern $E_2$ of eight spots X. Throughout the pattern, adjacent spots are separated by an angle $\beta_2$ of 45°. The pattern is arranged such that a set $S_3$ of two spots is located on the major axis $M_1$ and a set $S_4$ of two spots is located on the minor axis $M_2$. The two spots in each set are arranged symmetrically with respect to the major and minor axes. The spots in sets $S_3$ and $S_4$ are located a radial distance $R_3$ and $R_4$, respectively, from the center point $P_2$. $R_3$ and $R_4$ are defined by and may be determined from the equation for the ellipse $E_2$. The four remaining spots are arranged along the ellipse $E_2$ and positioned along lines $B_1$ and $B_2$ that are offset from the major and minor axes by the angle $\beta_2$. As shown, these four spots are arranged symmetrically with respect to the major and minor axes, with two of the spots positioned along line $B_1$ and the other two spots positioned along $B_2$. Each of these four spots in set $S_5$ is located a radial distance $R_5$ from center point $P_2$, and thus, in a circular pattern having radius $R_5$.

If an elliptical treatment pattern of 16 spots is desired, the patterns of two eight-spot ellipses, such as those of FIGS. 4A and 4B, may be combined. Once the elliptical treatment plan pattern is developed, the user may treat the eye using circular patterns of spots of varying radii, such as $R_1$ and $R_2$ and/or $R_3$, $R_4$ and $R_5$, permitting radiation delivery from certain spots in the circular pattern and preventing radiation delivery from other spot locations in the circular pattern, as described above. Preferably, the treatment includes one exposure using one circular pattern, followed by another exposure using another circular pattern, until the treatment according to the elliptical treatment pattern is finished. By way of example, the elliptical treatment patterns of FIGS. 4A and 4B may be carried out with two exposures (two lines in the display region 621 of FIG. 2) and three exposures (three lines in the display 621), respectively, where one exposure is used for each set of spots. The 16-spot elliptical treatment pattern that includes the patterns of FIGS. 4A and 4B may be carried out with five exposures (five lines in the display 621). This ellipse-based treatment is substantially uniform with respect to each treatment step, substantially symmetrical, and can be carried out in few steps.

An elliptical radiation pattern, whether the pattern of spots being described herein, a continuous radiation pattern or otherwise, results in unequal changes in the curvature of an exposed cornea along the two axes of the ellipse. Since the radiation along the short (minor) axis is close to the center of the eye, it has a greater effect in steepening the slope of the corneal surface in that direction than the radiation along the long (major) axis that is further removed from the eye's center. Thus, the minor axis is oriented in a direction along a flatter portion of the cornea's surface, while the major axis is positioned across steeper portions.

It will be understood that additional elliptical patterns may be added to the final treatment pattern, such as an elliptical pattern fitting within, surrounding, or overlapping an elliptical pattern described above. Indeed, a pattern of two ellipses with their major and minor axes aligned but of different values, is useful. The amount of correction brought about by such a double elliptical pattern may, as one example, be controlled by the fixing the major and minor axes of a larger of the two ellipses and then adjusting the major and minor axes of the smaller ellipse.

Another example pattern shown in FIG. 4C is termed a "bow-tie" pattern. Two or more spots, in this case three spots, are arranged together on opposite sides of a center $P_4$ along two lines that pass through that center. This pattern is formed by the instrument of FIG. 1 with three successive exposures of spots in concentric circles of different diameters, all but the four spots shown on each of the circles of FIG. 4C being blocked by their respective apertures during each exposure.

While three pre-defined spot patterns have been described above, there are many patterns that may be developed to treat the eye of a patient. For example, the user may add or subtract individual spots or a group of spots from a pattern, such as the circular, elliptical and bow-tie patterns described above. Alternately, the user may place individual spots in the treatment region to form a more arbitrary treatment pattern. Also, the pre-defined spot patterns will be recognized as being symmetrical about a center of the circular patterns used to form them. Certain treatments, however, require non-symmetrical patterns to formed, where the pre-defined patterns are altered by adding or subtracting spots, as an example. Indeed, the eye represented by the topographical display in the region 603 (FIG. 2) has a non-symmetrical shape which requires a non-symmetrical pattern of radiation spots to reshape its corneal surface into a preferred spherical surface that is symmetrical about the center of the eye.

The user may enter certain pre-operative data for use in developing a treatment plan, as described above. For example, the user may import images of the patient eye, such as topographical, pachymetric, or other diagnostic images, for use in developing a treatment plan. The image is imported from the image source to the Treatment Plan screen described above. Several images may be so imported. The user may simply pull up an image for viewing it during the preparation of a treatment plan. Alternately, the user may place spots of a treatment plan pattern on one of these images, or on a grid system, using a graphical user interface. The spots may be placed anywhere in the treatment region, and thus, are not confined to placement on grid lines or the like.

FIG. 5 is a flow-chart illustrating a method of importing and manipulating images in the Treatment Plan screen. The image of FIG. 5 is called a "Left Image" or "Left" when it will appear in the left box 603 of the screen of FIG. 2, and a "Right Image" or "Right" when it will appear in the right box 605. Although the flow-chart of FIG. 5 specifies only the Left Image, it will be recognized that the same process occurs to select and use the Right Image. For convenience, the word "Image" is used alone in this description to indicate an image, wherever it appears on the Treatment Plan screen.

The steps illustrated in the flow-chart illustration of FIG. 5 are carried out using the interactive tools of the system, in a known manner. For example, the method of using and manipulating an image, as illustrated in FIG. 5, is described in terms of pulling down, typing, selecting from drop-down lists, pointing, clicking, activating up and down arrows, and the like. It will be understood that any of a variety of interactive methods and tools may be used.

As illustrated in FIG. 5, in a first step 5-0, the user pulls down the View menu on the Treatment Plan screen and selects a box that provides choices for viewing an image from which a selection may be made. The user may then choose, in a step 5-2 to open an image, in response to which the system prepares to open, in a step 5-4, one of the image boxes 603 or 605. The user will select an image file (step 5-6) by typing a file name in an input data field, picking a name from a drop-down list, or otherwise interacting with the system. If the system is able to open the selected image file, the image from the file is displayed in the viewing box (step 5-8) and the name of the selected file is displayed in the data field (step 5-10). This displaying of information may occur simultaneously, or in an order other than that shown.

The user may choose to save an image (step 5-12), in response to which the system prepares to save an image screen (step 5-14). The user will select an image file (step 5-16) by typing a file name in an input data field, picking a name from a drop-down list, or otherwise interacting with the system. If the system is able to save the selected image file, the image file is copied to the systems main disk drive or a local disk under the selected name (step 5-18) and the name of the selected file, if saved, is displayed in a data field (step 5-20).

The user may wish to zoom (in size) in or out on an image displayed in one of the boxes 603 or 605 for better or selective viewing, in which case he or she activates the zoom image function (step 5-22) using the interactive tools of the system. The system responds by displaying an input data field for a numeric zoom value (step 5-24). The user then enters a zoom value (step 5-26), for example, by clicking on an up or down arrow (under the boxes 603 and 605 in FIG. 2) to increase or decrease a default zoom value appearing in the data field using an interactive tool. The system responds by zooming in or out on the original image (step 5-28), such that the zoomed image is a magnification or de-magnification of the original image, according to the zoom value specified.

The user may wish to zoom (in location) to a certain part of the image, in which case he or she activates the zoom center-point function (step 5-30) using the interactive tools of the system. The system responds by displaying a message that prompts the user to point to desired center point of the image and click on that point (step 5-32). The user points and clicks (step 5-34), whereupon the system displays at least part of the image surrounding the selected center point (step 5-36). The user may return to the center point of the original image, by clearing the selected center point (step 5-38). The system responds by displaying the original image according to the original center point (step 5-40). The user may want to clear the image altogether. To do so, he or she will activate the clear image function (step 5-42) and the system will respond by clearing the image from the image box (step 5-44) in which it was displayed.

As mentioned above, the user may develop a treatment plan pattern using an image or several images imported into the Treatment Plan screen or a grid. The grid may take a variety of forms, such as a bull's-eye-type grid having a center and concentric circles therearound, a graph-paper-type grid having parallel lines in vertical and horizontal directions, and the like. By way of example, a default grid may include a center point marked by cross-hairs and concentric circles therearound at the boundaries of the desired treatment region. This is what is shown in the image box 605 of the Treatment Plan screen of FIG. 2.

The Treatment Plan screen has an interactive planning area, such as the right image box 605, into which the user may import an image (such as a topographic representation of the patient eye before treatment) or into which the system may automatically place a default grid. The user may interact with the image or grid to develop a treatment plan pattern using interactive tools. For convenience, the Treatment Plan screen has a button bar 631 (FIG. 2) from which the user may select certain drawing tools to develop the radiation spot pattern if automatic calculation of the pattern is not used. For ease in use, the button bar is placed in the vicinity of the interactive planning area, immediately along side of the right box 605. Preferably, the buttons in the button bar 631 have easily identifiable icons which relate to the feature provided upon activation of the button, such as a single-circle icon on a top button 631*a* to be activated for generating a single-circle pattern as shown in the image box 605, a double circle on a second button 631*b* from the top for generating a pattern on two circles, such as shown in FIG. 3, an ellipse on a third button 631*c* from the top for generating an elliptical pattern of dots, such as shown in FIGS. 4A and 4B, a bow tie on a fourth button 631*d* for generating the pattern shown in FIG. 4C, and so on.

The user first selects one of the available patterns by activating one of the buttons of the button bar 631, and then individually locates and positions spots of a desired radiation treatment pattern across the screen box 605, preferably by using a background drawing shape (not shown) as a guide. More than one background shape may be selected, either at the same time or in sequence during formation of the treatment plan.

A method of developing a treatment plan pattern is illustrated in the flow chart of FIG. 6. The user first activates the appropriate function from the Tool pull down menu (step 6-0), with an activating click or the like. Some features of the treatment plan pattern will be automatically generated based on system defaults and/or preference settings, as further described herein. For example, typically, the system default will be set for an 8-spot treatment plan pattern. If the user wants 16 spots in the treatment plan, he or she may select that feature (step 6-2), for example, by checking a selection box 630 (FIG. 2) which appears in the Treatment Plan screen. Spots in each circular pattern are then generated in two exposures with the spots rotated by one-half the angular distance between spots, in this case 22.5 degrees, between exposures. The user's selection becomes the default for the circles of spots from which various patterns are formed.

The user can activate a single circle pattern (step 6-4) by clicking on a single-circle button 631*a* of the button bar 631. The system will respond by drawing in the display box 605 a circle with 8 (as shown) or 16 spots (step 6-6), as set by a system default and/or a preference setting. The spot pattern generated is then automatically selected for further editing (step 6-38). A similar interaction is used to generate a pattern in the display box 605 of spots in two concentric circles having different diameters (step 6-10), as shown in FIG. 3, by activating the two-circles button 631*b* (step 6-8). Similarly, a pattern of spots in an ellipse (step 6-12) is created in the display box 605 by pressing the ellipse button 631*c* (step 6-14). In response to pressing one of these buttons, the spot pattern is automatically selected for further editing (step 6-38).

A bow-tie button 631*d*, which is the fourth from the top of the button bar 631 (step 6-16), a line button 631*e* (step 6-20), or spot button 631*f* (step 6-24) may be activated to generate a bow-tie pattern (step 6-18) of FIG. 4C, a line pattern (step 6-22), or a single spot (step 6-26), having characteristics of the system default and/or preference settings. The bow-tie and line patterns may include 4, 8, or 12 spots. The user may also select a spot-fill button 631*g*, seventh from the top (step 6-28), whereupon the system responds with symmetrical and asymmetrical user-selection buttons (step 6-30). The user must select one of these buttons (step 6-32). After this selection, the user clicks on a starting point in the interactive planning area and moves the trackball or mouse to an ending point (step 6-34). The system responds by automatically filling in spots from the starting point to the end point (step 6-36), according to a system default and/or preference setting, symmetrically or asymmetrically, according to the user selection. As with the other patterns, any bow-tie, line, single-spot, or spot-fill pattern will be automatically selected for editing (step 6-38). Two or more of the pre-configured patterns may be selected and displayed at the same time.

The user may edit any of the patterns generated and displayed in the foregoing manner, by using various edit buttons appearing in the button bar. The user simply pulls down the Tool menu (step 6-0) described above, and selects an edit button, such as a "Move", "Select", "Delete", or "Delete All" button. Once the user selects the Move button (step 6-42), he or she then clicks on a spot in the pattern and, via trackball or mouse, drags that spot to a more desirable location. The spot thus becomes repositioned (step 6-46). When the user selects the Select button (step 6-48), he or she then clicks on an individual spot or selects a pattern (step 6-50). The system responds with the numeric fields corresponding to that spot or that pattern (step 6-52), as described below in connection with FIG. 7.

The user may select the Delete button (step 6-54) to delete a selected spot or pattern (step 6-62). The system may be adapted to require the user to go through the selection function described above to select the spot of pattern to be deleted. Alternately, the user clicks on a spot or pattern (step 6-56), whereupon the system deletes the selected subject matter (step 6-62). The user may select the Delete All button (step 6-58), whereupon the system deletes all spots and patterns (step 6-60).

This technique thus enables the user to enter or import diagnostic information, such as refractive data or imported topographic or pachymetric maps of the eye, and to develop a treatment plan pattern, such as a previously stored pattern or a newly generated pattern, based on the diagnostic information. For example, the user may develop a treatment plan pattern by placing spots over the imported image in the interactive image screen box 605 by using the graphical, drawing and editing tools, as described above. Once the user has developed the treatment plan pattern, the system is triggered to specify parameters of one or more exposures to spots in the available circular pattern that form the designed treatment plan pattern.

A "Preference Settings" feature is now described. The system software is responsive to a user's input, for example, the user's development of a spot pattern. The software refines that input according to its algorithms, values, defaults, and the like, to generate preference settings. These preference settings may be viewed by the user in a Preference Settings screen, which is preferably interactive so that the user may change some of the preference settings, if so desired. The preference settings may include a range of diameter values for a circular pattern, from a minimum to a maximum value, such as from 5 mm to 9.5 mm. This preference setting corresponds to the preferred treatment region of the patient eye, namely, a region bounded by concentric circles, centered on the eye, the inner circle and outer circle having the minimum and the maximum diameter value, respectively. This preferred treatment zone excludes the central optical zone where treatment is not desired. A default treatment zone setting may be from a diameter of 4.5, 5.0 or 5.5 mm to about 8.5 mm. As this preference setting is based on a typical or average human eye, a user may adjust the setting, for example, if the patient has a non-typical eye. Adjustment of this and other preference settings may be accomplished by user interaction with edit features in the Preference Setting screen. For example, the system may be set up to allow the user to click on an "up"-arrow or a "down"-arrow feature or icon to increase or decrease a value in the Preference Settings screen.

The preference settings may include information for specific patterns, such as ellipse, circle, and double-circle patterns, that are selectable from the button bar 631. For example, for an ellipse pattern, the effective diameter on the minor axis $M_2$ (FIGS. 4A and 4B) may be set at 5.5 mm, while that on the major axis $M_1$ may be set at 9.0 mm. Further by way of example, for a single-circle pattern, the circle diameter may be set at 8.0 mm, and for a double-circle pattern, the inner and outer circle diameters may be set at 6.0 mm and 7.0 mm, respectively. The preference settings may include energy and pulse information, such as a default energy per spot value and a default number of pulses. An energy per spot value of 23 mJ is an example of a possible default preference setting. An example of a default pulse number value is one. Preferably, the user may interact with the system to adjust the preference settings just described.

The preference settings may include defaults for a line pattern that is selected by activating the button 631e of the button bar 631. For example, the line pattern may have a default number of pairs of spots, such as two or three. A line pattern having two pairs of spots may be described in relation to FIG. 3, wherein the line pattern includes line L extending from the center P through two spots $X_1$ and dashed line $L_M$ that mirrors line L and goes through two spots $X_M$ that mirror the two spots $X_1$. The innermost spots $X_1$ and $X_M$ relative to center point P form one pair of spots, while the remaining spots form the other pair of spots. The preference settings may include a default diameter value for the first pair of spots, such as 6.0 mm, and another for the second pair of spots, such as 7.0 mm. Preferably, the default number of pairs of spots and the default diameter value for each pair may be adjusted by the user.

The system software is designed to optimize the treatment plan pattern under development. The preference settings may include a default tolerance value for optimization of the pattern selected by the user. That is, the software will optimize the treatment plan pattern, such that the above-described aspects of the pattern, such as number of pulses, fall within a range of the preference setting±the default tolerance value. Preferably, the default tolerance value may be adjusted by the user. If the values appearing in the Preference Settings screen are acceptable to the user, he or she may accept same interactively, such as by clicking on an "OK" feature or icon, or save same in a table file in a known manner.

Once the treatment pattern has been designed, the system software specifies parameters of one or more separate exposures, to be made in sequence on the cornea or other tissue being treated. The parameters of each exposure for a particular designed treatment are displayed in the exposure (optimization) table 621 (FIG. 2), as described above. Since the instrument of FIG. 1 only generates multiple spots in a circular pattern, two or more exposures to selected spots with different geometric parameters are most commonly made in order to expose the cornea or other tissue surface to the designed treatment plan pattern. The numbers and specifics of the exposures that form each of several of common patterns are described above. The system software references a table when an elliptical pattern is specified by the user, for example, to obtain default parameters of each of multiple circular spot pattern exposures that forms the specified ellipse.

FIG. 7 is a flow chart illustration of a method for changing parameters of a selected treatment plan spot or pattern. As illustrated in FIG. 6 and described above, the user may activate the Select function (step 6-48) to select a spot or pattern (step 6-50) and view the numeric fields corresponding to the selected spot or pattern (step 6-52) in a display field 635 (FIG. 2). These numeric fields correspond to the real-time preference settings generated by the system as just described. Preferably, a display field 635 of the Treatment Plan screen (FIG. 2) provide the values of these numeric fields for the selected pattern where the user is interactively developing a treatment pattern.

If the user wants to change a numeric field, he or she may activate a "Numeric Fields Options" function (step 7-0) from the Tools pull down menu, as shown in FIG. 7, and interact with the system to change that field by changing the values displayed in the display field 635 of the Treatment Screen (FIG. 2). For example, the user may interactively change a diameter value (step 7-2), an angle α value (step 7-4), an energy/spot value (step 7-6), and ellipse X value relative to the major axis $M_1$ (step 7-8) or the ellipse Y minor axis $M_2$ (step 7-10). The display field 635 may provide user-interactive features or icons, such as the up-arrow and down-arrow icons shown for value incrementation and decrementation, respectively. If a change is made, the values for the selected spot or pattern (step 7-12) and the image screen (step 7-14) are updated by the system.

An optimization (exposure step) table, described below, is updated by the system (step 7-16), as well. Preferably, the optimization table appears in the Treatment Plan screen area 621, as previously described, where the user is interactively generating or has so generated a treatment plan pattern. During this process, the system responds with a table, or optimization table, update, as shown in FIGS. 6 (step 6-40) and 7 (step 7-16). Preferably, the optimization table is a table-form arrangement of the display fields shown in Column 2 of the "System Display Fields" table of FIG. 8. While the fields may be displayed in any order or table format, it is preferable to arrange the fields in columns, starting with a column for the step (exposure) numbers and rows thereebeneath displaying the step number, beginning with the first step of the pattern. The remaining information will then be displayed in adjacent columns, with the information displayed in rows therebeneath, wherein the information in a particular row corresponds to the step number displayed at the beginning of that row. By way of example, the table may be of the form illustrated in region 621 of the Treatment Plan screen (FIG. 2) with columns for displaying the energy, such as the energy per spot, the pulses, such as the number of pulses, the effective pattern diameter at the patient eye, the angle α, and the spots that are "on" and "off" in the pattern. As to the latter, the column may be split into 8 or 16 sub-columns, with crosses ("x"s) or dashes ("-"s) under "on" spots or "off" spots, respectively. A "Desired Correction" value will also be displayed in the Treatment Plan screen in display field 623, typically, apart from the optimization table.

Other data may be displayed in the Treatment Plan screen, such as that shown in Columns 1 and 3 of the table of FIG. 8. For example, the total treatment time, total energy, and total number of spots for the treatment plan pattern may be displayed, in any desirable format. The system automatically generates this data from the data in the optimization table. Further by way of example, pre-operative data described above, such as the sphere, cylinder, vertex, and spherical equivalent, whether manifest, cycloplegic, or auto-cycloplegic, may be displayed in the Treatment Plan screen in any desirable format.

The user may interact with the optimization table and the Desired Correction feature, as illustrated by the flow chart of FIG. 9. Typically, for this interaction, the user goes to the optimization table options (step 9-0) in the Treatment Plan screen. By way of example, the options feature may be in the form of an "up"-scroll feature and a "down"-scroll feature that the user may click on. Typically, the line or row including data corresponding to the first step (exposure) in the pattern will be the default position that is highlighted in the display field 621 (FIG. 2). When the user clicks on the "up" feature or arrow (step 9-2) that is to the right of the display region 621, a line or row in the table is selected that is one line or row higher than the highlighted position (step 9-4). If the highlighted position is the row corresponding to the first step in the treatment and there is no further "up" position, the highlighted position will not be changed. When the user clicks on the "down" feature or arrow (step 9-6), a line or row in the table is selected that is one line or row lower than the highlighted position. If the highlighted position is the row corresponding to the last step in the treatment and there is no further "up" position, the highlighted position will not be changed. If the default position or highlighted position is where the user wants it to be, no "up" or "down" editing is required.

Once a line or treatment step is highlighted according to the user's preference, the system will automatically display in the region 623 a desired correction value (diopters) corresponding to the selected treatment step. This desired correction value is generated by the system software. If the user wishes to change the desired correction value, he or she may change it using an interactive tool, such as an increment/decrement feature. The system will respond by automatically updating the energy value of that treatment exposure (step 9-12), according to the system software, and displaying the updated energy value in the optimization table (step 9-14).

FIG. 10 is a flow chart illustration of various menu options 10-0 available to the user to accomplish the many of the foregoing treatment planning steps and methods. The user may go to the Treatment Plan screen to open a pre-existing treatment or optimization table (step 10-2), for example, by using an "Open" feature to open a previously saved table file. The system will respond by displaying an open image screen (step 10-4) and an interactive device for selecting a file, such as a drop-down menu for file selection from a list of available files. The user may then select a file (step 10-6), for example, by scrolling within the list and highlighting a file name in the list in a known manner. The system will respond by reading the treatment plan pattern data in the selected file (step 10-8), and drawing or displaying the treatment plan pattern image (step 10-10) in the region 621 of the Treatment Plan screen (FIG. 2). The system then generates or updates the optimization table for that treatment plan pattern (step 10-12).

The user may also go to the Treatment Plan screen to save a treatment plan table (step 10-14) or an image (step 10-22). The system will respond by displaying a save screen (step 10-16) or a save image screen (step 10-24), respectively. The user may then select a file (step 10-18) or (step 10-22), respectively. The system will respond by saving treatment plan table data (step 10-20) or image data (step 10-24), respectively. The user may also go to the Treatment Plan screen to view the Preference Settings screen (step 10-26), in response to which the system will display that screen (step 10-28).

An example of computer software to implement the foregoing is provided in source code in the above-referenced microfiche appendix that is being filed herewith and forms a part of this description. This source code is subject to copyright protection by Sunrise Technologies International, Inc., assignee of the present application. The copyright owner has no objection to the facsimile reproduction by anyone of the appendix, as it appears in the Patent and Trademark Office patent file or records, but otherwise reserves all copyright rights whatsoever.

Although the various aspects of the present invention have been described with respect to the preferred embodiments thereof, it will be understood that the invention is entitled to protection within the full scope of the appended claims.

It is claimed:

1. A method of forming and utilizing a pattern of radiation spots, comprising:

forming a desired pattern of spots on a display screen of a processor, breaking up the desired pattern of spots into at least first and second component patterns of spots that individually include respective first and second numbers of less than all of a set number of spots equally spaced around circles having a common center and respective first and second diameters that are different from one another, and thereafter directing radiation according to at least said first and second component patterns of spots in time succession onto a surface of biological tissue.

2. The method of claim 1, wherein forming the desired pattern of radiation spots includes forming an elliptical pattern of said radiation spots, and wherein said first component pattern of spots provides spots along opposing long sides of the ellipse and said second component pattern of spots provides spots along opposing short sides of the ellipse, said second diameter being greater than said first diameter.

3. The method of claim 1, wherein forming the desired pattern of radiation spots includes forming an elliptical pattern of said radiation spots, and wherein said first component pattern of spots provides spots along opposing long sides of the ellipse, said second component pattern of spots provides a pair of spots along the opposing long sides of the ellipse, and a third component pattern of spots having less than all of the set number of spots equally spaced around another circle having the common center provides a pair of spots along the opposing short sides of the ellipse, a third diameter of the third component pattern of spots being greater than said second diameter.

4. The method of claim 1, wherein forming the desired pattern includes positioning at least two spots on opposite sides of said center on a line passing through said center, and wherein said first component pattern of spots provides a first pair of said at least two spots on opposite sides of said center and said second component pattern of spots provides a second pair of said at least two spots on opposite sides of said center.

5. The method of claim 1, wherein forming the desired pattern includes positioning at least two spots on opposite sides of said center on each of at least first and second lines that pass through said center and form an acute angle with each other, and wherein said first component pattern of spots provides a first pair of said at least two spots on opposite sides of said center on each of said first and second lines and said second component pattern of spots provides a second pair of said at least two spots on opposite sides of said center on each of said first and second lines.

6. The method of any one of claims 1–5, wherein the set number of spots is four or more.

7. The method of claim 6, wherein the set number of spots is exactly eight.

8. The method of any one of claims 1–5, wherein directing radiation onto a surface of biological tissue includes exposing a surface of an eye's cornea to at least said first and second component patterns of spots in time succession with a level of energy that shrinks collagen tissue within the cornea with a pattern according to said desired pattern of spots in a manner to reshape the cornea surface.

* * * * *